(12) United States Patent
Tabor et al.

(10) Patent No.: US 10,030,099 B2
(45) Date of Patent: *Jul. 24, 2018

(54) DIGESTION OF KERATIN

(71) Applicant: Resinate Materials Group, Inc., Plymouth, MI (US)

(72) Inventors: Rick Tabor, Plymouth, MI (US); Eric David Vrabel, Ferndale, MI (US); Matthew J Beatty, Ann Arbor, MI (US); Jack Rogers Kovsky, Detroit, MI (US)

(73) Assignee: Resinate Materials Group, Inc., Plymouth, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/084,737

(22) Filed: Mar. 30, 2016

(65) Prior Publication Data
US 2017/0029551 A1 Feb. 2, 2017

Related U.S. Application Data

(63) Continuation of application No. PCT/US2015/045798, filed on Aug. 19, 2015.

(60) Provisional application No. 62/039,816, filed on Aug. 20, 2014, provisional application No. 62/039,820, filed on Aug. 20, 2014, provisional application No. 62/082,974, filed on Nov. 21, 2014, provisional application No. 62/110,343, filed on Jan. 30, 2015, provisional application No. 62/110,347, filed on Jan. 30, 2015, provisional application No. 62/185,008, filed on Jun. 26, 2015.

(51) Int. Cl.
| | | |
|---|---|---|
| *C08G 18/28* | (2006.01) | |
| *C08G 63/91* | (2006.01) | |
| *C08G 63/183* | (2006.01) | |
| *C08G 18/66* | (2006.01) | |
| *C08G 18/72* | (2006.01) | |
| *C09D 175/04* | (2006.01) | |
| *C08J 11/24* | (2006.01) | |
| *C07C 29/09* | (2006.01) | |
| *C07C 31/18* | (2006.01) | |
| *C08G 18/08* | (2006.01) | |
| *C08J 9/14* | (2006.01) | |
| *C08F 20/10* | (2006.01) | |
| *C08G 18/42* | (2006.01) | |
| *C08G 18/76* | (2006.01) | |
| *C09D 5/03* | (2006.01) | |
| *C09D 175/06* | (2006.01) | |
| *C08G 101/00* | (2006.01) | |

(52) U.S. Cl.
CPC ............ *C08G 63/916* (2013.01); *C07C 29/09* (2013.01); *C07C 31/18* (2013.01); *C08F 20/10* (2013.01); *C08G 18/14* (2013.01); *C08G 18/28* (2013.01); *C08G 18/4213* (2013.01); *C08G 18/664* (2013.01); *C08G 18/722* (2013.01); *C08G 18/7671* (2013.01); *C08G 63/183* (2013.01); *C08J 9/141* (2013.01); *C08J 11/24* (2013.01); *C09D 5/03* (2013.01); *C09D 175/04* (2013.01); *C09D 175/06* (2013.01); *C08G 2101/00* (2013.01); *C08G 2101/0025* (2013.01); *C08G 2150/20* (2013.01); *C08J 2203/14* (2013.01); *C08J 2205/10* (2013.01); *C08J 2367/02* (2013.01); *C08J 2375/04* (2013.01); *Y02W 30/706* (2015.05)

(58) Field of Classification Search
CPC ......... C07C 29/09; C07C 31/18; C08F 20/10; C08G 18/14; C08G 18/28; C08G 18/4213; C08G 18/664; C08G 18/722; C08G 18/7671; C08G 63/183; C08G 63/916; C08G 2101/00; C08G 2101/0025; C08G 2150/20; C08J 9/141; C08J 11/24; C08J 2203/14; C08J 2205/10; C08J 2367/02; C08J 2375/04; C09D 5/03; C09D 175/04; C09D 175/06

See application file for complete search history.

(56) References Cited

U.S. PATENT DOCUMENTS

| | | | |
|---|---|---|---|
| 4,197,353 A | 4/1980 | Tobias et al. | |
| 4,266,027 A | 5/1981 | Muller et al. | |
| 4,520,139 A | 5/1985 | Crehan et al. | |
| 4,873,268 A | 10/1989 | Hallmark et al. | |
| 4,876,304 A | 10/1989 | Mertz et al. | |

(Continued)

FOREIGN PATENT DOCUMENTS

| | | |
|---|---|---|
| CA | 2216772 | 4/1998 |
| CN | 102516593 | 6/2012 |

(Continued)

OTHER PUBLICATIONS

Thacker et al. "Antidegradants", Handbook of Vinyl Formulating, 2008. pp. 77-78.

(Continued)

*Primary Examiner* — John Cooney
(74) *Attorney, Agent, or Firm* — Dilworth IP, LLC

(57) ABSTRACT

The present invention relates to the chemical digestion of keratin, such as avian feathers and wool. The digestion product is made by heating the feathers or wool with a solvent selected from glycols, alkanolamines, polyamines, and combinations thereof. The resulting digested keratin product is a keratin-derived polyol useful for making polymeric materials such as polyurethanes. The digestion products provide a sustainable alternative to petrochemical based intermediates.

18 Claims, No Drawings

(56) References Cited

U.S. PATENT DOCUMENTS

| | | | |
|---|---|---|---|
| 5,068,395 | A | 11/1991 | Bathe |
| 5,147,926 | A | 9/1992 | Meichsner et al. |
| 5,294,729 | A | 3/1994 | Wicks et al. |
| 5,319,128 | A | 6/1994 | DuPont et al. |
| 5,612,467 | A | 3/1997 | Weuthen et al. |
| 5,637,654 | A | 6/1997 | Panandiker et al. |
| 5,763,692 | A | 6/1998 | Kierkus et al. |
| 5,922,474 | A | 7/1999 | Kuo |
| 5,968,992 | A | 10/1999 | Naber et al. |
| 6,069,182 | A | 5/2000 | Naber et al. |
| 6,750,260 | B2 | 6/2004 | Sendijarevic |
| 7,030,057 | B2 | 4/2006 | Matsumoto |
| 7,659,320 | B2 | 2/2010 | Berard |
| 7,902,264 | B2 | 3/2011 | Determan et al. |
| 8,344,172 | B2 | 1/2013 | Tabor et al. |
| 8,530,626 | B1 * | 9/2013 | Cardamone ........ C07K 14/4741 530/350 |
| 8,546,519 | B2 | 10/2013 | Selifonov et al. |
| 8,604,077 | B2 | 12/2013 | Wicks et al. |
| 8,680,227 | B1 | 3/2014 | Bell et al. |
| 8,692,013 | B2 | 4/2014 | Tabor et al. |
| 2004/0102533 | A1 | 5/2004 | Durand et al. |
| 2006/0025544 | A1 | 2/2006 | Koube et al. |
| 2006/0089453 | A1 | 4/2006 | Pajerski |
| 2007/0225473 | A1 | 9/2007 | Determan et al. |
| 2008/0194713 | A1 | 8/2008 | Kim et al. |
| 2009/0131625 | A1 | 5/2009 | Kurian et al. |
| 2009/0234034 | A1 | 9/2009 | Blanco |
| 2010/0204392 | A1 | 8/2010 | Marsh et al. |
| 2011/0039959 | A1 | 2/2011 | Kim et al. |
| 2012/0035376 | A1 | 2/2012 | Mullen et al. |
| 2012/0118201 | A1 | 5/2012 | Mullen et al. |
| 2012/0121911 | A1 | 5/2012 | Mullen et al. |
| 2013/0072628 | A1 | 3/2013 | Crawford et al. |
| 2014/0060383 | A1 | 3/2014 | Wu et al. |
| 2014/0163127 | A1 | 6/2014 | Selifonov et al. |

FOREIGN PATENT DOCUMENTS

| | | |
|---|---|---|
| CN | 103030796 | 4/2013 |
| CN | 102061009 | 10/2013 |
| EP | 1693409 | 8/2006 |
| EP | 25652261 | 3/2013 |
| ES | 2277554 | 7/2008 |
| JP | 04189881 | 7/1992 |
| JP | 2000198876 | 7/2000 |
| JP | 2004161666 | 6/2004 |
| JP | 2004168811 | 6/2004 |
| JP | 2004168812 | 6/2004 |
| JP | 2004238581 | 8/2004 |
| JP | 2005002161 | 1/2005 |
| PL | 212329 | 9/2012 |
| WO | 2004005365 | 1/2004 |
| WO | 2007062118 | 5/2007 |
| WO | 2008085397 | 7/2008 |
| WO | 2009032905 | 3/2009 |
| WO | 2009048874 | 4/2009 |
| WO | 2009049041 | 4/2009 |
| WO | 2010075330 | 7/2010 |
| WO | 2010151558 | 12/2010 |
| WO | 2011138432 | 11/2011 |
| WO | 2012065116 | 5/2012 |
| WO | 2013154874 | 10/2013 |
| WO | 2014023684 | 2/2014 |
| WO | 2014027104 | 2/2014 |
| WO | 2014075051 | 5/2014 |

OTHER PUBLICATIONS

You et al.,"Chemical Recycling of Polyurethanes and Applications for the Recyclates", BASF Corporation, pp. 363-374.
International Search Report and Written Opinion mailed in PCT/US2015/057685 dated Jan. 29, 2016.
You et al., A New Era of Polyurethane Recycling—Fascia to Roof Rail: Sustainable Recycling in Automotive , Polyurethanes Expo (1999), pp. 377-382.
von Stein et al., "Salt-assisted Organic-acid-catalyzed depolymerization of cellulose", Green Chem. (2010) 12, 1844-1849.
Viana et al. "Chemical Recycling of PET by Catalyzed Glycolysis: Kinetics of the Heterogeneous Reaction", Chem. Eng. Journ. 173 (2011) 210-219.
Saucedo-Rivalcoba et al., "(Chicken feathers keratin)/polyerathane membranes", Appl. Phys. A (2011) 104:219-228.
Pierson et al., "Acid-Catalyzed Chitin Liquefaction in Ethylene Glycol", ACS Publications (2014) 2081-2089.
Shukla et al., "Zein, the Industrial Protein from Corn", Industrial Crops and Products 13 (2001) 171-192.
Kelsey et al. "High Impact, Amorphous Terephthalate Copolyesters of Rigid 2,2,4,4-Tetramethyl-1,3-cyclobutanediol with Flexible Diols", Macromolecules (2000), 33, 5810-5818.
Sun, "Enzymatic Hydrolysis of Soy Proteins and the Hydrolysates Utilisation", Int. Journ. of Food Science and Technology (2011), 46, 2447-2459.
Ullah et al., "Bioplastics from Father Quill", BioMacromolecules, ACS (2011), 3826-3832.
Frisch, "Progress in Recycling of Polyurethanes", Polimery (1998) 43, No. 10, 579-660.
Bouchard, et al. "Characterization of Depolymerized Cellulosic Residues", Wood Sci. Technol. (1990) 24: 159-169.
Lee et al., "Desaminated Glycolysis of Water-Blown Rigid Polyurethane Foams", Journal of Applied Polymer Science, vol. 77, (2000) 2646-2656.
"Fuel from Chicken Feathers?", www.alternative-energy-news.infofuel-from-chicken-feathers.pdf, Dec. 3, 2015.
Buggy et al. "Recovery of Polyol from Flexible Polyurethane Foam Wastes", Key Engineering Materials vols. 99-100 (1995) pp.65-78.
Nagase et al., "Development of a Chemical Recycling Process for Waste Plastics Using Supercritical Water", Kobelco Technology Review No. 22, (Apr. 1999) 11-14.
Nikles et al., "New Motivation for the Depolymerization Products Derived from Poly(Ethylene Terephthalate) (PET) Waste: a Review", Macromol. Mater. Eng., (2005) 290, 13-30.
Sigma Product Information Sheet, "Zein from Maize", MWM/RXR, Oct. 2003.
Bartecka, et al., "Polyols Obtained from Chemical Recycling of Integral Polyurethanes Waste Used for the Production of Urethane-rubber Composites", Modern Polymeric Materials for Environmental Applications, vol. 3, (2008), pp. 5-8.
Zahedi et al. "Optimization of Phthalic/Maleic Anhydride-Endcapped PET Oligomers using Response Surface Method", Polymer Engineering and Science (2014), 419-429.
Mazurek et al. "PET Wastes utilization in the synthesis of aliphatic-aromatic polyurethane elastomers", Polym. Adv. Technol., (2014) 25, 1273-1284.
Kim et al., "Kinetics of Polycarbonate Glycolysis in Ethylene Glycol", Ind. Eng. Chem. Res. (2009), 48, 685-691.
Oku et al., "Chemical conversion of poly(carbonate) to bis(hydroxyethyl) ether of bisphenol A. An Approach to the chemical recycling of plastic wastes as monomers", Polymer 41 (2000) 6749-6753.
Wicks, Jr., et al., "Powder Coatings", Organic Coatings: Science and Technology, Third Ed., (2007) 548-571.
Tavano, "Protein hydrolysis using proteases: An important tool for food biotechnology", Journal of Molecular Catalysis B: Enzymatic 90 (2013) 1-11.
Datta, "Effect of glycols used as glycolysis agents on chemical structure and thermal stability of the produced glycolsyates", J. Therm. Anal. Calorim (2012) 109:517-520.
Chun et al. "Characterization and Improvement of the Recyclate Obtained from the Glycolysis Reaction of Waste MDI Based Polyurethane Foam", Polyurethane Con. 2000, Oct. 8-11, 2000 537-541.
Nikje et al. "Polyurethane Waste Reduction and Recycling: From Bench to Pilot Scales", Designed Monomers and Polymers 14:5 (2011) 395-421.

(56) References Cited

OTHER PUBLICATIONS

Sendijarevic et al., "Chemical Recycling of Mixed Polyurethane Foam Stream Recovered from Shredder Residue into Polyurethane Polyols", Journal of Cellular Plastics, vol. 43 (Jan. 2007) 30-46.
Molero et al., "Chemical recovery of flexible polyurethane foam wastes", WIT Transactions on Ecology and the Environment, vol. 140, (2010) pp. 69-81.
Molero et al., "Influence of the Use of Recycled Polyols Obtained by Glycolsysis on the Preparation and Physical Properties of Flexible Polyurethane", Journal of Applied Polymer Science, vol. 109 (2008) pp. 617-626.
Ulrich, "Recent Advances in Polyisocyanurate Technology", Int. Conf. (1980): Cellular and non-Cellular Polyurethanes; pp. 81-89.
Ritter, "BPA is Indispensible for Making Plastics" ACS—Chem. Eng. vol. 89, No. 23, (2011).
Leaversuch, "Thermoplastic Polyesters; It's a Good Time to Know Them Better", Plastics Technology, (Jun. 2004), pp. 46-51, 63-64.
European Commission Joint Research Centre "Survey of technologies for the recycling by chemolysis", (May 1996), IPTS, pp. 1-41.
Sun "Enzymatic hydrolysis of soy proteins and the hydrolysates utilisation", International Journal of Food Science and Technology (2011), 46, pp. 2447-2459.
Saint-Loup et al. "Synthesis of (polyethylene terephthalatefpolye-caprolactone) copolyesters", Polymer 44, (2003) 3437-3449.
Mulder, "Proteins in Biomass Streams" Biorenewable Resources Platform, (Apr. 2010), 60 pages.
Schmid et al. "Thermoforming of whey protein-based barrier layers for application in food packaging", FS&T, vol. 25, Issue 3, (2011) pp. 34-35.
Floris et al., "Application of whey proteins as coating ingredients", NUTRAfoods (2010), 9(4) pp. 25-31.
Burkhart, "Silicone Surfactants, Unique Additives to Optimize Polyurethane Foam Manufacturing", 60 Years of Polyurethanes, International Symposium and Exhibition (1998) p. 375.
Boehme et al, "Synthesis and characterization of a novel unsaturated polyester based on poly(trimethylene)", Polymer (2006), 47(6), 1892-1898 CODEN: POLMAG; ISSN: 0032-3861.
Raudenbusch, "A novel concept for crosslinking surface coatings", Organic Coatings (1984), 7, 59-78 CODEN: ORGCD8; ISSN: 0883-2676 (abstract).
Ronda et al. "A renewable approach to thermosetting resins" Reactive & Functional Polymers (2013), 73(2), 381-395 CODEN: RFPOF6; ISSN: 1381-5148.
Zhang et al. "Study of liquefaction of wood and its components in polyhydric alcohol" Linehan Huaxue Yu Gongye (2012), 32(2), 14-20 CODEN: LHYGD7; ISSN: 0253-2417.
Lin, Recycling Technology of Poly(ethylene Terephthalate) Materials; Macromol. Symp. 135, (1998) 129-135.
International Search Report mailed in PCT/US2015/045972 dated Oct. 27, 2015, 3 pages.
International Search Report mailed in PCT/US2015/045978 dated Nov. 25, 2015, 5 pages.
Das et al. "Production of biofuel from chicken feathers" Int Journ. Power Eng and Energy (2013), 4:2; pp. 364-366.
Martelli, et al. "Chicken feather keratin films plasticized with polyethylene glycol" Int. Jour. Poly. Mat Poly. Biomat. (2012), vol. 61, 1, pp. 17-29.
Wang et al. "A high-capacity carbon prepared from renewable chicken feather biopolymer for supercapacitors" Journ. Power Sources (2013) vol. 225, pp. 101-107.
Flores-Hernandez et al. "All green composites from fully renewable biopolymers: Chitosan-starch reinforced with keratin from feathers" Polymers (2014), vol. 6, No. 3 pp. 686-705.
Kim et al. "Kinetics of Polycarbonate Glycolysis in Ethylene Glycol", Ind. Eng. Chem. Res. (2009), 48, pp. 685-691.

\* cited by examiner

US 10,030,099 B2

DIGESTION OF KERATIN

RELATED APPLICATIONS

This application is a continuation U.S. Application under 35 U.S.C. § 365 of International Patent Application No. PCT/US2015/045798, filed on Aug. 19, 2015, which claims priority to U.S. Provisional Patent Application Ser. No. 62/039,816 filed on Aug. 20, 2014, U.S. Provisional Patent Application Ser. No. 62/039,820 filed on Aug. 20, 2014, U.S. Provisional Patent Application Ser. No. 62/082,974 filed on Nov. 21, 2014, U.S. Provisional Patent Application Ser. No. 62/110,343 filed on Jan. 30, 2015, U.S. Provisional Patent Application Ser. No. 62/110,347 filed on Jan. 30, 2015, and U.S. Provisional Patent Application Ser. No. 62/185,008 filed on Jun. 26, 2015, the disclosures of each of which are incorporated herein by reference in their entirety.

FIELD OF THE INVENTION

The present invention relates to the chemical digestion of keratin, such as avian feathers and wool. Keratin is a family of fibrous structural proteins that are known for being both hard and tough at the same time. It is the key structural component of animal feathers, wool, hair, nails, and horns. The digestion product is made by heating the keratin source with a solvent, such as glycols, alkanolamines, and polyamines, and combinations thereof. The resulting digested digestion product is a versatile keratin-derived polyol useful for making polymeric materials such as polyurethanes. The digestion products provide a sustainable alternative to petrochemical based intermediates.

BACKGROUND OF THE INVENTION

As manufacturers increasingly seek to offer products with improved sustainability, the availability of intermediates produced from bio-renewable and/or recycled materials becomes more leveraging. However, there remains a need for these products to deliver equal or better performance than their traditional petroleum-based alternatives at a comparable or lower price point.

Bio-renewable content alone can be misleading as an indicator of "green" chemistry. For example, when a food source such as corn is needed to provide the bio-renewable content, there are clear trade-offs between feeding people and providing them with performance-based chemical products. Additionally, the chemical or biochemical transformations needed to convert proteins, carbohydrates, or other bio-friendly feeds to useful chemical intermediates and products can consume more natural resources and energy, and can release more greenhouse gases and pollutants into the environment than their petro-based alternatives in the effort to achieve "green" status.

The safe disposal or reuse of waste materials from various sources is an environmental and economic challenge. Such wastes had typically gone into landfills, but as landfill capacity is becoming ever scarcer and disposal costs are continuously increasing, cost effective and environmentally acceptable alternatives are needed to deal with these waste materials. Waste streams are produced by a great range of industries and sources, including, e.g., the plastics industry, the automobile industry, the paper industry, consumers, the agricultural industry, including both crop and animal production, as well as the production of animal products (e.g., the meat, dairy, egg, and wool industries). Because of these environmental and cost challenges, there is a need to find practical uses for recycled polymers and waste streams. In other words, there is the need to utilize recycled polymers and waste streams to produce new polymers and building blocks for these new polymers.

The domestic poultry and egg industries produce a large amount of waste products such as feathers and down feathers. Bird feathers such as chicken feathers, chicken down, duck feathers, duck down, goose feathers, goose down, turkey feathers, and turkey down, are an abundant and renewal source of keratin. It is known that avian feathers can be formed into thermoplastic compositions by extrusion with glycol plasticizers and reducing agents such as sodium sulfite. Further, it is known that avian feathers can be partially hydrozlyed to form animal feedproducts or glycolyzed at high pressures with nontoxic, edible polyols in the presence of a feather degradation agent to form animal feed products. In this feed product technology, the polyols used are limiting relative to the final properties needed for an industrial polyol. See Bumla, N. A., et al., *Process and Utilization of Feathers*, Poultry Technology, Jul. 28, 2012; V. Saucedo-Rivalcoba, et al., (*Chicken feathers keratin)/polyurethane membranes*, Applied Physics A (2011) 104: 219-228; A. Ullah, et al., *Bioplastics from Feather Quill*, Biomacromolecules 2011, 12 3826-3832; U.S. Pat. No. 4,908,220, to Shih et al., issued Mar. 13, 1990; US Patent Application Publication No. US 2014/0060383 A1, to Wu et al., published Mar. 6, 2014; and PCT Patent Application Publication No. WO 2014/023684 A1, to Nestec S. A., published Feb. 13, 2014; which are all incorporated by reference herein in their entirety. There is a need to develop methods for utilizing this source of keratin for making industrial polyol intermediates that allow for a broad variety of polymer performance attributes in the final polymer application.

Industrial polyols are commonly used intermediates for the manufacture of condensation and addition polymers. These condensation and addition polymers include polyurethane products such as flexible and rigid polymeric foams, polyisocyanurate foams, coatings, sealants, adhesives, and elastomers. Additional condensation and addition polymers include polyester polyol intermediates that can be sued to make the above mentioned polyurethane and polyisocyanurate products. These industrial polyols depend on chemical attributes such as hydroxyl functionality, branching, linearity, hydrophobe content, aromatic content, aliphatic content, polyether content, hydrogen bonding, crystallinity, glass transition, melting point, and various other chemical features to provide the full range of performance benefits to the final polymer into which they are incorporated. The use of only edible glycols or polyols for the digestion of the keratin is a severe limitation to the range of properties and costs available to non-edible glycols, and additionally creates economic competition between food sources and performance industrial chemicals at a time when the world needs more affordable and available food sources.

It is apparent from the above there is an ongoing need for sustainable sources of polymeric materials which a help to reduce waste streams and provide further options for the use of under-utilized raw materials while at the same time avoiding the competition for raw materials that can be used both as food sources and performance industrial chemicals.

SUMMARY OF THE INVENTION

The present invention relates to the chemical digestion of keratin, such as avian feathers. The digestion product is made by heating the feathers with a solvent, such as glycols, alkanolamines, and polyamines. The resulting digested digestion product is a keratin-derived polyol useful for making polymeric materials such as polyurethanes. The digestion products provide a sustainable alternative to petrochemical based intermediates.

We surprisingly found that keratinous materials such as avian feathers can be digested with glycol materials to prepare polyols, and in particular that the glycol materials can include inedible glycols materials, using mild reaction conditions at atmospheric pressure to prepare industrial poloyls.

High-recycle-content polyols having desirable hydroxyl numbers, viscosities, and other attributes useful for formulating polyurethane products can be made by reacting, at certain equivalent ratios, a glycol and a keratin source, such as keratin from avian feathers. The polyols, which are valuable for formulating a variety of polyurethanes and related products—including polyurethane dispersions, flexible and rigid polymeric foams, coatings, adhesives, sealants, and elastomers—provide a sustainable alternative to bio- or petrochemical-based polyols.

DETAILED DESCRIPTION OF THE INVENTION

The present invention relates to a polyol, particularly a keratin-derived polyol, comprising recurring units of: (a) a glycol, an alkanolamine, a polyamine, or combinations thereof, and (b) an intermediate made by digesting a keratin source.

In one aspect the present invention relates to a keratin-derived polyol comprising recurring units generated from: (a) a glycol, an alkanolamine, a polyamine, or combinations thereof, and (b) a keratin source.

In another aspect the present invention relates to a keratin-derived polyol comprising recurring units of: (a) a glycol, and (b) an intermediate made by digesting a keratin source.

In another aspect the present invention relates to a keratin-derived polyol comprising recurring units generated from: (a) a glycol, and (b) a keratin source.

In another aspect the present invention relates to a keratin-derived polyol comprising recurring units of: (a) an alkanolamine, and (b) an intermediate made by digesting a keratin source.

In another aspect the present invention relates to a keratin-derived polyol comprising recurring units generated from: (a) an alkanolamine, and (b) a keratin source.

In another aspect the present invention relates to a keratin-derived polyol comprising recurring units of: (a) a polyamine, and (b) an intermediate made by digesting a keratin source.

In another aspect the present invention relates to a keratin-derived polyol comprising recurring units generated from: (a) a polyamine, and (b) a keratin source.

In another aspect the present invention relates to a keratin-derived polyol made by a process comprising heating a glycol, an alkanolamine, a polyamine, and combinations thereof, with a keratin source.

In another aspect the present invention relates to a keratin-derived polyol made by a process comprising heating a glycol with a keratin source.

In another aspect the present invention relates to a keratin-derived polyol made by a process comprising heating an alkanolamine with a keratin source.

In another aspect the present invention relates to a keratin-derived polyol made by a process comprising heating a polyamine with a keratin source.

In another aspect the present invention relates to a keratin-derived polyol wherein the process further comprises heating in the presence of a catalyst.

In another aspect the present invention relates to a keratin-derived polyol according wherein the glycol is selected from ethylene glycol, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexanedimethanol, diethylene glycol, tetraethylene glycol, dipropylene glycol, triethylene glycol, tripropylene glycol, polyethylene glycol, polypropylene glycol, erythritol, pentaerythritol, sorbitol, and block or random copolymer glycols of ethylene oxide and propylene oxide, or combinations thereof.

In another aspect the present invention relates to a keratin-derived polyol wherein the glycol is selected from ethylene glycol, propylene glycol, diethylene glycol, and polyethylene glycol.

In another aspect the present invention relates to a keratin-derived polyol wherein the glycol is selected from ethylene glycol, diethylene glycol, and low molecular weight polyethylene glycol.

In another aspect the present invention relates to a keratin-derived polyol wherein the glycol is diethylene glycol.

In another aspect the present invention relates to a keratin-derived polyol wherein the polyethylene glycol is a low molecular weight polyethylene glycol.

In another aspect the present invention relates to a keratin-derived polyol wherein the low molecular weight polyethylene glycol has a molecular weight of less than about 2000.

In another aspect the present invention relates to a keratin-derived polyol wherein the low molecular weight polyethylene glycol has a molecular weight of less than about 1000.

In another aspect the present invention relates to a keratin-derived polyol wherein the low molecular weight polyethylene glycol has a molecular weight of less than about 600.

In another aspect the present invention relates to a keratin-derived polyol wherein the glycol is an inedible glycol.

In another aspect the present invention relates to a keratin-derived polyol wherein the glycol is an industrial glycol solvent.

In another aspect the present invention relates to a keratin-derived polyol wherein the glycol is a recycled glycol.

In another aspect the present invention relates to a keratin-derived polyol that is an industrial polyol.

In another aspect the present invention relates to a keratin-derived polyol wherein the alkanolamine is selected from ethanolamine, diethanol amine, triethanol amine, N-alkyl diethanolamine, isopropanolamine, diisopropanol amine, triisopropanol amine, N-alkyl diisopropanol amine, N-alkyl ethanolamine, 1,4-bis(2-hydroxyethyl)piperazine, 1-(2-hydroxyethyl)piperazine, fatty alkyl alkanol amines, 1-(2-(n, n-bis-(2-hydroxypropyl)-amino)-ethyl)-4-(2-hydroxypropyl)-piperazine, 1,4-bis(2-hydroxypropyl)piperazine, mono or polyalkoxylates of ethylene diamine, N,N-bis(2-hydroxyethyl)ethylenediamine, N,N,N,N-tetrakis(2-hydroxyethyl)ethylenediamine, alkoxylates of hexanediamine, alkoxylates of polyamines, alkoxylates of butanediamine, 1-(2-hydroxypropyl)piperazine, alkoxylates of toluene diamine, alkoxylates of aniline, alkoxylates of methylene dianiline, Mannich polyols by the Mannich reaction between a phenol or alkyl phenol, formaldehyde and alkanol amines, alkoxylates of melamine, and Mannich polyols obtained by the reaction of melamine with formaldehyde and a dialkanolamine, and combinations thereof.

In another aspect the present invention relates to a keratin-derived polyol wherein the polyamine is selected from ethylene diamine, diethylene triamine, triethylene tetraamine, tetraethylene pentaamine, piperazine, 1-(2-aminoethyl)piperazine, polyoxyalkyleneamines (for example, Jeffamine™ products containing an average functionality of 1.5 or more amine groups per molecule), 1,4-bis(2-aminoethyl)piperazine, butanediamine, hexanediamine, dimer diamine (for example, Priamine™ 1074, supplied by Croda), diaminocyclohexane, norbornane diamine, 1,12-dodecanediamine, 1,10-decanediamine, isophorone diamine, and diethyl toluene diamine, and combinations thereof.

In another aspect the present invention relates to a keratin-derived polyol wherein the keratin source is selected from avian feathers, wool, and combinations thereof.

In another aspect the present invention relates to a keratin-derived polyol wherein the keratin source is selected from avian feathers.

In another aspect the present invention relates to a keratin-derived polyol wherein the avian feathers are selected from vaned feathers and down feathers, or combinations thereof.

In another aspect the present invention relates to a keratin-derived polyol wherein the keratin is derived from feather meal.

In another aspect the present invention relates to a keratin-derived polyol wherein the avian feathers are selected from chicken feathers, chicken down feathers, turkey feathers, turkey down feathers, duck feathers, duck down feathers, goose feathers, goose down feathers, and combinations thereof.

In another aspect the present invention relates to a keratin-derived polyol wherein the avian feathers are chicken feathers.

In another aspect the present invention relates to a keratin-derived polyol wherein the avian feathers are chicken down feathers.

In another aspect the present invention relates to a keratin-derived polyol wherein the avian feathers are turkey feathers.

In another aspect the present invention relates to a keratin-derived polyol wherein the avian feathers are turkey down feathers.

In another aspect the present invention relates to a keratin-derived polyol wherein the avian feathers are duck feathers.

In another aspect the present invention relates to a keratin-derived polyol wherein the avian feathers are duck down feathers.

In another aspect the present invention relates to a keratin-derived polyol wherein the avian feathers are goose feathers.

In another aspect the present invention relates to a keratin-derived polyol wherein the avian feathers are goose down feathers.

In another aspect the present invention relates to a keratin-derived polyol wherein the keratin source is selected from wool.

In another aspect the present invention relates to a keratin-derived polyol wherein the keratin source and the glycol, alkanolamine, or polyamine are heated at a temperature within the range of about 70° C. to about 240° C.

In another aspect the present invention relates to a keratin-derived polyol wherein the keratin source and the glycol, alkanolamine, or polyamine are heated at atmospheric pressure.

In another aspect the present invention relates to a keratin-derived polyol wherein the keratin source and the glycol are heated at a pressure from about 5 psia to about 75 psia.

In another aspect the present invention relates to a keratin-derived polyol having a hydroxyl number within the range of about 10 to about 800 mg KOH/g.

In another aspect the present invention relates to a keratin-derived polyol having a hydroxyl number within the range of about 25 to about 500 mg KOH/g.

In another aspect the present invention relates to a keratin-derived polyol having a hydroxyl number within the range of about 35 to about 400 mg KOH/g.

In another aspect the present invention relates to a keratin-derived polyol having a hydroxyl number within the range of about 50 to about 400 mg KOH/g.

In another aspect the present invention relates to a keratin-derived polyol having an acid number of less than 10 mg KOH/g.

In another aspect the present invention relates to a keratin-derived polyol having a viscosity at 125° C. less than about 5000 cP.

In another aspect the present invention relates to a keratin-derived polyol having a viscosity at 25° C. less than about 20,000 cP.

In another aspect the present invention relates to a keratin-derived polyol having a viscosity at 25° C. less than about 10,000 cP.

In another aspect the present invention relates to a keratin-derived polyol having a keratin source content as defined herein greater than 3 wt %.

In another aspect the present invention relates to a keratin-derived polyol further comprising a hydrophobe or nonionic surfactant, or combinations thereof In another aspect the present invention relates to a keratin-derived polyol wherein the hydrophobe or nonionic surfactant is selected from ricinoleic acid, castor oil, ethoxylated castor oil, saturated or unsaturated C9-C18 dicarboxylic acids, vegetable oils, fatty acids, fatty acid esters, modified vegetable oils, fatty triglycerides, cardanol-based products, recycled cooking oil, isostearyl alcohol, hydroxy-functional materials derived from epoxidized, ozonized, or hydroformylated fatty esters, dimer fatty acids, block copolymers of ethylene oxide with propylene oxide, alkoxylated alkyl phenols, alkoxylated fatty alcohols, or combinations thereof.

In another aspect the present invention relates to a polyurethane made from the keratin-derived polyols of the present invention.

In another aspect the present invention relates to a polyurethane comprising a keratin-derived polyol of the present invention.

In another aspect the present invention relates to an aqueous polyurethane dispersion made from the keratin-derived polyols of the present invention.

In another aspect the present invention relates to an aqueous polyurethane dispersion comprising a keratin-derived polyol of the present invention.

In another aspect the present invention relates to a coating made from the keratin-derived polyols of the present invention.

In another aspect the present invention relates to a coating comprising a keratin-derived polyol of the present invention.

In another aspect the present invention relates to a coating according wherein the coating is selected from liquid coatings and powder coatings.

In another aspect the present invention relates to a liquid coating comprising a keratin-derived polyol of the present invention.

In another aspect the present invention relates to a liquid coating wherein the coating comprises from 1% to 95% by weight of the keratin-derived polyol.

In another aspect the present invention relates to a liquid coating that is a polyurethane coating.

In another aspect the present invention relates to a powder coating comprising a keratin-derived polyol of the present invention.

In another aspect the present invention relates to a powder coating wherein the coating comprises from 1% to 95% by weight of the keratin-derived polyol of the present invention.

In another aspect the present invention relates to a powder coating having at least one glass transition temperature, Tg, greater than or equal to 45° C.

In another aspect the present invention relates to a powder coating having at least one melting point greater than or equal to 45° C.

In another aspect the present invention relates to a powder coating further comprising a crosslinking agent, a flow control agent, a degassing agent, and a catalyst.

In another aspect the present invention relates to a powder coating further comprising a pigmenting material.

In another aspect the present invention relates to a metal substrate coated with the coating material of the present invention.

In another aspect the present invention relates to a polymeric foam made from the keratin-derived polyol of the present invention.

In another aspect the present invention relates to a polymeric foam comprising a keratin-derived polyol of the present invention.

In another aspect the present invention relates to a polymeric foam that is a rigid polyurethane foam.

In another aspect the present invention relates to a polymeric foam that is a polyisocyanurate foam.

In another aspect the present invention relates to an acrylate or polyacrylate made from the keratin-derived polyols of the present invention.

In another aspect the present invention relates to an acrylate or polyacrylate comprising a keratin-derived polyol of the present invention.

In another aspect the present invention relates to a process for making a digestion product from a keratin source comprising heating a keratin source with a digesting material selected from a glycol, an alkanolamine, or a polyamine, or combinations thereof, to give a digested product.

In another aspect the present invention relates to a process for making a digestion product from a keratin source wherein the digesting material further comprises an aromatic polyacid source, an aliphatic polyacid source, or combinations thereof.

In another aspect the present invention relates to a process for making a digestion product from a keratin source wherein the digesting material further comprises an aromatic polyacid source.

In another aspect the present invention relates to a process for making a digestion product from a keratin source wherein the digesting material further comprises an aliphatic polyacid source.

In another aspect the present invention relates to a keratin-derived polyol having a viscosity at 125° C. less than about 5000 cP.

In another aspect the present invention relates to a keratin-derived polyol having a viscosity at 25° C. less than about 20,000 cP.

In another aspect the present invention relates to a keratin-derived polyol having a viscosity at 25° C. less than about 10,000 cP.

Definitions

As used herein, the following terms have the indicated meanings unless expressly stated to the contrary:

The term "aminolysis" as used herein is from the field of polymer chemistry where it refers to the digestion of a polymer with an amino compound, for example an alkanolamine or polyamine, to yield lower molecular weight fragments, such as for example, oligomers and monomers.

The term "digestible polymer" as used herein to a polymer component of the processes and compositions of the present invention that is capable of being broken down or degraded into smaller polymeric, oligomeric, or monomeric components via a chemical reaction. An example of a chemical reaction in which the digestible polymer is digested or broken down is glycolysis. A variety of digestible polymers are useful herein, with the present invention focusing on the proteinaceous material, keratin. The source of these polymers, that is, the keratin source can be procured from feathers as a waste or byproduct from the poultry and egg industries.

The term "glycolysis" as used herein is from the field of polymer chemistry where it refers to the digestion of a polymer with a glycol to yield lower molecular weight fragments, such as for example, oligomers and monomers.

The term "inedible" as used herein and referring in certain embodiments to the glycol digesting materials, means a glycol that is not considered as a food additive or as Generally Recognized as Safe (GRAS) in the United States for human consumption. See, http://www.fda.gov/Food/IngredientsPackagingLabeling/FoodAdditivesIngredients/ucm228269.

The terms "waste stream" as used herein refers to waste or discarded products from industry, agriculture, or consumer sources that has few ultimate destinations or applications other than for example, landfill, incineration, animal feed, concrete, burning as a source of energy, fertilization, landscaping mulch, or other relatively low value applications.

Digestible Polymers

The polyol compositions and processes of the present invention comprise a digestible polymer, or polymeric material such as the protein, keratin. This polymer is referred to as the keratin source, which is digested as described herein. Of particular interest in the present invention is keratin from avian feathers and wool from animals.

The keratin source can be digested using a glycol in a process called glycolysis. In other embodiments, the keratin source can be digested with an amine such as an alkanolamine or a polyamine in a process called aminolysis.

The keratin-derived polyols can be prepared by reacting a glycol with a keratin source at temperatures between about 50° C. and about 260° C., preferably at temperatures between about 70° C. and about 240° C., and most preferably at temperatures between about 90° C. and about 235° C. Generally, the reaction is run at atmospheric pressure, although the reaction can be run at pressures between about 0 psia to about 100 psia, about 5 psia to about 75 psia, and about 7 psia to about 65 psia. In the instances where it is desirable to remove water, reduced pressures below 1 atmosphere can be useful.

Also, as described herein and in the Example section, the polyols can be made in a one pot or one reactor system in which the digesting material and the keratin source are first reacted to provide a keratin-containing polyol, followed by combining further with an aromatic polyacid source such as, for example, a thermoplastic polyester. Examples of thermoplastic polyesters include polyethylene terephthalate (PET), polybutylene terephthalate, polytrimethylene terephthalate, glycol-modified polyethylene terephthalate, copolymers of terephthalic acid and 1,4-cyclohexanedimethanol, isophthalic acid-modified copolymers of terephthalic acid and 1,4-cyclohexanedimethanol, copolymers of 2,5-furandicarboxylic acid, or copolymers of 2,5-dialkyl 2,5, furandicarboxylates, or combinations thereof. A preferred thermoplastic polyester is recycled polyethylene terephthalate, due to its highly ready availability and sustainable nature.

Other aromatic polyacid sources are useful to further react with the keratin-derived polyol to form keratin-derived aromatic polyester polyols. Examples of materials that contain aromatic polyacid groups suitable for the practice of the invention include phthalic acid, phthalic anhydride, dimethyl phthalates, dialkyl phthalates, terephthalic acid, dimethyl terephthalates, dialkyl terephthalate, isophthalic acid, dimethyul isophthalates, dialkyl isophthalates, (dimethyl terephthalate) DMT bottoms (for examples as described in U.S. Pat. No. 5,075,417, to Trowell et al, issued Dec. 24, 1991; U.S. Pat. No. 4,897,429, to Trowell et al., issued Jan. 30, 1990; U.S. Pat. No. 3,647,759, to Walker et al, issued Mar. 7, 1972; U.S. Pat. No. 4,411,949, to Snider et al, issued Oct. 25, 1983; and U.S. Pat. No. 4,714,717, to Londrigan et al, issued Dec. 22, 1987; which are incorporated by reference herein in their entirety), trimellitc acid, trimellitic anhydride, tirmethyl trimelliatte, naphthalene dicarboxylic acid, pyromellitic anhydride, 2,5-furandicarboxylic acid, dialkyl 2,5-furandiarboxylates, pyromellitic acid, dimethyl naphthalene dicarboxylate, and mixtures thereof.

Also suitable for reacting with the keratin to produce keratin-derived polyols are aliphatic diacids, aliphatic anhydrides, and aliphatic half or diesters. Examples include maleic anhydride, succinic anhydride, succinic acid or its mono- or dialkyl esters, maleic acid or its mono- or dialkyl esters, fumaric acid or its mono- or dialkyl esters, azelaic acid or its mono- or dialkyl esters, adipic acid or its mono or dialkyl esters, malonic acid or its mono- or dialkyl esters, glutaric acid or its mono- or dialkyl esters, nonendioic acid or its mono- or dialkyl esters, sebacic acid or its mono- or dialkyl esters, decendioic acid or its mono- or dialkyl esters, dodecanedioic acid or its mono- or dialkyl esters, dodecenedioic acid or its mono- or dialkyl esters, tetradecanedioic acid or its mono- or dialkyl esters, tetradecenedioic acid or its mono- or dialkyl esters, hexadecanedioic acid or its mono- or dialkyl esters, hexadecendioic acid or its mono- or dialkyl esters, ocatdeancedioic acid or its mono- or dialkyl esters, octadecenedioic or its mono- or dialkyl esters, and the like, and mixtures thereof.

Keratin: Digestible Keratin Sources

Keratin belongs to the class of materials referred to as proteins. Proteins are naturally occurring polymeric materials made of amino acids linked together by peptide, i.e. amide groups. In other words, proteins are large biological molecules, or macromolecules, consisting of one or more long chains of amino acid residues. Proteins perform a vast array of functions within living organisms, including catalyzing metabolic reactions, replicating DNA, responding to stimuli, and transporting molecules from one location to another, and providing structure and mass to living organisms. Proteins differ from one another primarily in their sequence of amino acids, which is dictated by the nucleotide sequence of their genes, and which usually results in folding of the protein into a specific three-dimensional structure that determines its function and activity. Proteins are also found combined with fats and are referred to as lipoproteins and with polysaccharides and are referred to as glycoproteins.

Proteins are found in a wide variety of agricultural materials, plants, and animals. Proteins and their use as recycle or waste streams are further described in "Proteins in Biomass Streams: A study commissioned by the Biorenewable Resources Platform (Platform Groene Grondstoffen), authored by Wim Mulder and dated April 2010, which is incorporated by reference herein in its entirety. Examples of proteins include keratin, collagen, milk proteins such as casein and whey, zein, silk and wool.

Keratin is a family of fibrous structural proteins. Keratin is the key structural material making up the outer layer of human skin. It is also the key structural component of hair and nails. Keratin monomers are assembled into bundles to form intermediate filaments, which are tough and insoluble and form strong unmineralized tissues found in reptiles, birds, amphibians, and mammals. A form of keratin called alpha-keratin is composed of alpha-coils and globular sections, and is the main component of hair, wool, nails, horns, and hooves. A form of keratin called beta-keratin, in which the protein strands are hydrogen-bonded into pleated sheets are found in the feathers, beaks and claws of birds and the and the claws, scales and shells of reptiles. Silk is also an example of keratin.

A digestible polymer source useful herein is avian, i.e. bird, feathers, which include the tougher outer or vane (also vaned, vein, or veined) feathers of birds and the softer inner, or juvenile feathers (also called down or down feathers). The poultry, both meat and egg producing, industries generate a large amount of waste feathers and down. Thus bird feathers such as chicken feathers, chicken down, duck feathers, duck down, goose feathers, goose down, turkey feathers, and turkey down, are an abundant and renewal source of digestible keratin polymers. Furthermore, the feathers can be obtained in various processed and cleaned forms, including washed feathers, chopped feathers, and feather meal. See Bumla, N. A., et al., Process and Utilization of Feathers, Poultry Technology, Jul. 28, 2012; V. Saucedo-Rivalcoba, et al., (Chicken feathers keratin)/polyurethane membranes, Applied Physics A (2011) 104: 219-228; A. Ullah, et al., Bioplastics from Feather Quill, Biomacromolecules 2011, 12 3826-3832; and PCT Patent Application Publication No. WO 2014/023684 A1, to Nestec S. A., published Feb. 13, 2014; which have been cited above and incorporated by reference herein in their entirety. Feather meal is a byproduct of processing poultry. It is made from poultry feathers by partially hydrolyzing them under elevated heat and pressure, and then grinding and drying them. Although total nitrogen levels are fairly high (up to 12%), the bioavailability of this nitrogen may be low. Feather meal is used in formulated animal feed and as an organic fertilizer. Feather meal is made through a process called rendering. Steam pressure cookers with temperatures over 140° C. are used to "cook" and sterilize the feathers. This partially hydrolyzes the proteins, which denatures them. It is then dried, cooled and ground into a powder for use as a nitrogen source for animal feed (mostly ruminants) or as an organic soil amendment. In certain instances feather meal can be particularly well suited for digestion as it can digest more completely than whole feathers An additional example of keratin is wool. Wool is a textile fiber from sheep and certain other animals, including cashmere from goats, mohair from goats, qiviut from muskoxen, angora from rabbits, and other types of wool from camelids.

It should be noted that the Digestible Keratin sources as described herein in this section are considered separate from and are a distinct component of the present invention, from the Aromatic Polyacids sources as described in the Polyacid Source section, below.

Digesting Materials

The present invention utilizes a digesting material or solvent for digesting or solubilizing the keratin. Suitable materials include glycols, alkanolamines, and polyamines, and combinations of the foregoing.

Glycols

Glycols suitable for use are well known. By "glycol," we mean a linear or branched, aliphatic or cycloaliphatic compound or mixture of compounds having two or more hydroxyl groups. Other functionalities, particularly ether or ester groups, may be present in the glycol. In preferred glycols, two of the hydroxyl groups are separated by from about 2 to about 20 carbons, preferably from about 2 to about 14 carbon atoms, and more preferably from about 2 to about 8 carbons. Note that ether linkages may be included in the carbon separation between hydroxyl groups, though the oxygen atoms are not included in the carbon count. Suitable glycols include, for example, ethylene glycol, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexane-dimethanol, diethylene glycol, dipropylene glycol, triethylene glycol, 1,6-hexanediol, tripropylene glycol, tetraethylene glycol, polyethylene glycols (PEGs), polypropylene glycols (PPGs), erythritol, pentaerythritol, sorbitol, and block or random copolymer glycols s of ethylene oxide and propylene oxide, and the like, and mixtures thereof. Preferably, the glycol is selected from ethylene glycol, propylene glycol, 2-methyl-1,3-propanediol, diethylene glycol, 3-methyl-1,5-pentanediol, neopentyl glycol, and polyethylene glycols with molecular weights less than about 2000 (e.g., PEG 1000 and PEG 600), and mixtures thereof. Propylene glycol is particularly preferred. In a preferred aspect, the glycol is a recycled glycol, especially recycled propylene glycol and recycled diethylene glycol. Propylene glycol recovered from used deicing fluids is one example. In another preferred aspect, the glycol is a recycled ethylene glycol, which may be recovered from used engine antifreeze or coolant.

The glycols described herein can also be characterized for certain embodiments of the invention as inedible glycols and industrial glycols.

As described above, the term "inedible" as used herein and referring in certain embodiments to the glycol digesting materials, means a glycol that is not considered as a food additive or as Generally Recognized as Safe (GRAS) in the United States for human consumption. See, http://www.fda.gov/Food/IngredientsPackagingLabeling/FoodAdditivesIngredients/ucm228269. Examples of such inedible solvents include ethylene glycol, diethylene glycol, 1,2-butylene glycol, 1,4-butanediol, 2-methyl-1,3-propanediol, neopentyl glycol, 3-methyl-1,5-pentanediol, 1,4-cyclohexane-dimethanol, 1,3-cyclohexane-dimethanol, diethylene glycol, 1,6-hexanediol, tripropylene glycol and the like, and mixtures thereof.

Industrial glycols are those glycol materials that are produced and used in industrial processes such as manufacturing, vehicle and aircraft deicing, and heat transfer solvents, to name a few applications. Industrial glycols suitable for use are well known. Suitable industrial glycols include, for example, ethylene glycol, propylene glycol, 1,3-propanediol, 1,2-butylene glycol, 1,3-butylene glycol, 1,4-butanediol, 2-methyl-1,3-propanediol, neopentyl glycol, glycerol, trimethylolpropane, 3-methyl-1,5-pentanediol, 1,4-cyclohexane-dimethanol, 1,3-cyclohexane-dimethanol, diethylene glycol, dipropylene glycol, triethylene glycol, 1,6-hexanediol, tripropylene glycol, tetraethylene glycol, polyethylene glycols having a number average molecular weight up to about 400 g/mol, and the like, and mixtures thereof. Preferably, the glycol is selected from ethylene glycol, propylene glycol, 2-methyl-1,3-propanediol, 3-methyl-1,5-pentanediol, neopentyl glycol, diethylene glycol, polyethylene glycol having a number average molecular weight of about 200, and mixtures thereof. Propylene glycol is particularly preferred. In a preferred aspect, the glycol is a recycled glycol, especially recycled propylene glycol. Propylene glycol recovered from used deicing fluids is one example.

Alkanolamines and Polyamines

The keratin derived polyols may also be prepared by aminolysis or glycolysis of a keratin source such as, for example, feathers and wool, using amines such as alkanolamines or polyamines, or combinations thereof. For the purposes of this invention, in the instance where the alkanol amine is a tertiary alkanol amine, the process for digestion may also be classified as glycolysis. In the instance where the alkanol amine is a secondary or primary amine, the process may be classified as aminolysis. In the instance of polyamines, the digestion may be classified as aminolysis.

Amines useful herein for the aminolysis reaction are alkanolamines and polyamines.

Alkanolamines are organic compounds that contain both an amine functional group and an alcohol functional group. Examples of alkanolamines include ethanolamine, diethanol amine, triethanol amine, N-alkyl diethanolamine, isopropanolamine, diisopropanol amine, triisopropanol amine, N-alkyl diisopropanol amine, N-alkyl ethanolamine, 1,4-bis(2-hydroxyethyl)piperazine, 1-(2-hydroxyethyl)piperazine, fatty alkyl alkanol amines, 1-(2-(n,n-bis-(2-hydroxypropyl)-amino)-ethyl)-4-(2-hydroxypropyl)-piperazine, 1,4-bis(2-hydroxypropyl)piperazine, mono or polyalkoxylates of ethylene diamine, N,N-bis(2-hydroxyethyl)ethylenediamine, N,N,N,N-tetrakis(2-hydroxyethyl)ethylenediamine, alkoxylates of hexanediamine, alkoxylates of polyamines, alkoxylates of butanediamine, 1-(2-hydroxypropyl)piperazine, alkoxylates of toluene diamine, alkoxylates of aniline, alkoxylates of methylene dianiline, Mannich polyols by the Mannich reaction between a phenol or alkyl phenol, formaldehyde and alkanol amines (Chemistry and Technology of Polyols for Polyurethanes, Michail Ionescu, Rapra Technology Ltd., 2005, Chapter 15), alkoxylates of melamine, Mannich polyols obtained by the reaction of melamine with formaldehyde and a dialkanolamine (Chemistry and Technology of Polyols for Polyurethanes, Michail Ionescu, Rapra Technology Ltd., 2005, Chapter 15), and the like and mixtures thereof.

Polyamines are organic compounds that contain multiple amine functional groups. Examples of polyamines include ethylene diamine, diethylene triamine, triethylene tetraamine, tetraethylene pentaamine, piperazine, 1-(2-aminoethyl)piperazine, polyoxyalkyleneamines (for example, Jeffamine™ products containing an average functionality of 1.5 or more amine groups per molecule), 1,4-bis(2-aminoethyl)piperazine, butanediamine, hexanediamine, dimer diamine (for example, Priamine™ 1074, supplied by Croda), diaminocyclohexane, norbornane diamine, 1,12-dodecanediamine, 1,10-decanediamine, isophorone diamine, diethyl toluene diamine, and the like and mixtures thereof.

Polyacid Source

The present invention can further comprise a polyacid source, which can be selected from aromatic polyacid sources, aliphatic polyacid sources, and combinations thereof.

Aromatic Polyacid Source

The term "aromatic polyacid source" is used to designate that the material or source contains one or more aromatic acid moieties or groups. Chemical Struture 1, below, provides an illustration of an Aromatic Polyacid Source.

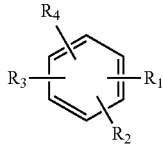

Chemical Structure 1

Where $R_1$ and $R_2$ are carboxylate groups; and $R_3$ and $R_4$ are selected from carboxylate group or hydrogen.

Chemical Structure 2, below provides another illustration of an Aromatic Polyacid Source.

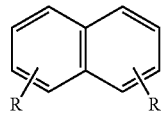

Chemical Structure 2

Where both R groups are carboxylic acid groups or alkyl ester groups.

Chemical Structure 3, below, provides another illustration of an Aromatic Polyacid Source.

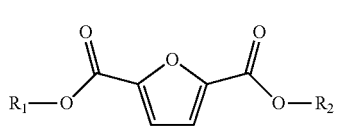

Chemical Structure 3

Where $R_1$ and $R_2$ are selected independently from either an alkyl group or hydrogen.

It should be noted that the Aromatic Polyacid source materials as described herein in this section are considered separate from and are a distinct component of the present invention, from the Digestible Keratin source, as described separately in the "Digestible Polymers" section, above.

The aromatic polyacid source includes polyesters such as thermoplastic polyesters. These include polyesters polymers prepared by the reaction of one or more difunctional and/or multifunctional aromatic carboxylid acids with one or more difunctional hydroxyl compounds and/or multifunctional hydroxyl compounds.

Examples of materials that contain aromatic polyacid groups suitable for the practice of the invention include phthalic acid, phthalic anhydride, dimethyl phthalates, dialkyl phthalates, terephthalic acid, dimethyl terephthalates, dialkyl terephthalate, isophthalic acid, dimethyl isophthalates, dialkyl isophthalates, dimethyl terephthalate (DMT) bottoms (for example, as described in U.S. Pat. No. 5,075,417, to Trowell et al, issued Dec. 24, 1991; U.S. Pat. No. 4,897,429, to Trowell et al., issued Jan. 30, 1990; U.S. Pat. No. 3,647,759, to Walker et al, issued Mar. 7, 1972; U.S. Pat. No. 4,411,949, to Snider et al, issued Oct. 25, 1983; and U.S. Pat. No. 4,714,717, to Londrigan et al, issued Dec. 22, 1987; which were cited above and incorporated by reference herein in their entirety), trimellitic acid, trimellitic anhydride, trimethyl trimellitate, naphthalene dicarboxylic acid, pyromellitic anhydride, 2,5-furandicarboxylic acid, dialkyl 2,5-furandicarboxylate, pyromellitic acid, dialkyl naphthalene dicarboxylate, and mixtures thereof.

Also, the term "terephthalic acid" is intended to include terephthalic acid itself and residues thereof as well as any derivative of terephthalic acid, including its associated acid halids, esters, half-esters, salts, half-stats, anhydrides, mixed anhydrides, or mixtures thereof or residues thereof useful in a reaction process with a diol to make a polyester.

Aromatic polyacid sources may also be obtained from thermoplastic polyesters. Thermoplastic polyesters suitable for use are well known in the art. They are condensation polymers produced from the reaction of glycols and aromatic dicarboxylic acids or acid derivatives. Examples include polyethylene terephthalate (PET), polybutylene terephthalate (PBT), polytrimethylene terephthalate (PTT), glycol-modified polyethylene terephthalate (PETG), copolymers of terephthalic acid and 1,4-cyclohexanedimethanol (PCT), copolymers of 2,5-furandicarboxylic acid or dialkyl 2,5-furandicarboxylate and at least one glycol, PCTA (an isophthalic acid-modified PCT), copolymers of naphthalene dicarboxylic acid or dialkyl naphthalene dicarboxylate and the like, and mixtures thereof.

Suitable thermoplastic polyesters include virgin polyesters, recycled polyesters, or mixtures thereof. Polyethylene terephthalate (PET) is particularly preferred, especially recycled polyethylene terephthalate (rPET), virgin PET, and mixtures thereof. For more examples of suitable thermoplastic polyesters, see U.S. Pat. Appl. Publ. No. 2009/0131625, the teachings of which are incorporated herein by reference.

Recycled polyethylene terephthalate suitable for use in making the inventive polyester polyols can come from a variety of sources. The most common source is the post-consumer waste stream of PET from plastic bottles or other containers. The rPET can be colorless or contain dyes (e.g., green, blue, brown, or other colors) or be mixtures of these. A minor proportion of organic or inorganic foreign matter (e.g., paper, other plastics, glass, metal, etc.) can be present. A desirable source of rPET is "flake" rPET, from which many of the common impurities present in scrap PET bottles have been removed in advance. Another desirable source of rPET is pelletized rPET, which is made by melting and extruding rPET through metal filtration mesh to further remove particulate impurities. Because PET plastic bottles are currently manufactured in much greater quantity than any recycling efforts can match, scrap PET will continue to be available in abundance. Other sources of PET include, PET textiles and PET carpeting, such as recycled PET textiles and recycled PET carpeting. For example, recycled PET polyester carpet including polyolefin backing, calcium carbonate filler, and latex adhesive, assuming an approximate PET composition of 90% of the carpet, is a useful source material to prepare the digested intermediate.

Polytrimethylene terephthalate (PTT) is another useful polyaromatic source, and like PET, can be obtained from PTT textiles and PTT carpeting, such as recycled PTT textiles and recycled PTT carpeting. For example, recycled PTT polyester carpet including polyolefin backing, calcium carbonate filler, and latex adhesive, assuming an approximate PTT composition of 90% of the carpet, is a useful source material to prepare the digested intermediate.

Other useful polyaromatic sources are polyesters made from polyaromatics and rigid diols such as cycloalkane diols, examples of such rigid diols including 2,2,4,4-tetramethyl-1,3-cyclobutanediol, 1,3-cycohexane diol, 1,4-cyclohexane diol, 1,3-cyclohexanedimethanol, and 1,4-cyclohexanedimethanol. Such examples include terephthalate copolyesters of 2,2,4,4-tetramethyl-1,3-cyclobutanediola, and also polyesters which also contain flexible diols, such as C2-C6 linear or branched aliphatic diols. Examples of these polyesters include, for example Eastman Tritan materials from post consumer recycle of water bottles See, also, U.S. Patent Application No. US 2013/0072628 A1, to Crawford et al., published Mar. 21, 2013; and D. R. Kelsey et al., *High Impact, Amorphous Terephthalate Copolyesters of Rigid 2,2,4,4-Tetramethyl*-1,3-*cyclobutanediol with Flexible Diols*, Macromolecules, 2000, 33, 5810-5818; which are incorporated by reference herein in their entirety.

Aliphatic Polyacid Source

As described above, also suitable for reacting with the keratin to produce keratin-derived polyols are aliphatic diacids, aliphatic anhydrides, and aliphatic half or diesters. Examples include maleic anhydride, succinic anhydride, succinic acid or its mono- or dialkyl esters, maleic acid or its mono- or dialkyl esters, fumaric acid or its mono- or dialkyl esters, azelaic acid or its mono- or dialkyl esters, adipic acid or its mono or dialkyl esters, malonic acid or its mono- or dialkyl esters, glutaric acid or its mono- or dialkyl esters, nonendioic acid or its mono- or dialkyl esters, sebacic acid or its mono- or dialkyl esters, decendioic acid or its mono- or dialkyl esters, dodecanedioic acid or its mono- or dialkyl esters, dodecenedioic acid or its mono- or dialkyl esters, tetradecanedioic acid or its mono- or dialkyl esters, tetradecenedioic acid or its mono- or dialkyl esters, hexadecanedioic acid or its mono- or dialkyl esters, hexadecendioic acid or its mono- or dialkyl esters, octadecanedioic acid or its mono- or dialkyl esters, octadecenedioic or its mono- or dialkyl esters, and the like, and mixtures thereof.

Hydrophobes and Nonionic Surfactants

The keratin-derived polyols of this invention may also comprise hydrophobes, nonionic surfactants, and mixtures thereof. Hydrophobes include triglycerides and modified triglycerides, fatty acids, fatty acid esters, dimer fatty acids, fatty diacids, vegetable oils and modified vegetable oils (for example as described in U.S. Pat. Nos. 5,922,779, 6,359,022, 6,664,363, and WO 2013/154874A1); castor oil (for example, as described in WO 2013/154874A1); modified or derivatized polyterpenes; modified cashew nut shell oil; cardanol; derivatives of cardanol; Diels Alder or ene reaction modified polyols (for example, as described in WO 2013/109834); and tall oil fatty acids (for example, as described in U.S. Pat. Nos. 5,075,417 and 4,897,429). The keratin-derived polyols may further comprise nonionic surfactants or reactants (for example, as described in U.S. Pat. No. 4,529,744, WO 9919377 and WO 2009045926).

Examples of triglycerides suitable for the practice of this invention include soybean oil, animal tallow, fish oil, canola oil, castor oil, tung oil, linseed oil, corn oil, recycled cooking oil, sunflower oil, palm oil, peanut oil, palm kernel oil, cottonseed oil, coconut oil, and safflower oil.

Examples of fatty acids suitable for the practice of this invention include linoleic, myristic, palmitic, caproic, caprylic, capric, 2-ethyl hexanoic, lauric, stearic, oleic, linolenic, ricinoleic, tall oil, and mixtures thereof. The alkyl esters of these fatty acids and mixtures of these alkyl esters thereof are also suitable examples for the practice of this invention.

Examples of fatty diacids suitable for the practice of this invention include azelaic acid; sebacic acid; dodecanedioic acid; tetradecanedioic acid; hexadecanedioic acid; octadecanedioic acid; nonene dioic acid; decenedioic acid, dodecenedioic acid; tetradecenedioic acid; hexadecenedioic acid; octadecenedioic acid; eicosendioic acid; eicosandioic acid; docosandioic acid; tetracosandioic acid; tetracosendioic acid; and the like and mixtures thereof.

Examples of nonionic surfactants include block copolymers of ethylene oxide with either propylene oxide, butylene oxide, or mixtures of propylene oxide with butylene oxide. See "nonionic Surfactants: Polyoxyalkylene Block Copolymers", (Surfactant Science Series, Book 60, CRC Press), 1996, Vaughn Nace, ed. And "Nonionic Surfactants: Organic Chemistry" (Surfactant Science Series Book 72), 1997 Nico M. van Os., ed. It is well known that initiators are used to initiate such block copolymers. Suitable initiators include glycols; monols; fatty alcohols; alkyl phenols; phenol; styrenated phenols; bisphenols; triols; and tetrols. An additional nonionic surfactant suitable for use as a reactant or additive includes ethoxylated or alkoxylated castor oil.

Catalysts

Although not specifically required, a catalyst can be used to catalyze the digestion reaction of the keratin source. Catalysts suitable for making the digested intermediate are well known (see, e.g., K. Troev et al., *J. Appl. Polym. Sci.* 90 (2003) 1148). In particular, suitable catalysts comprise titanium, zinc, antimony, germanium, zirconium, manganese, or other metals. Specific examples include titanium alkoxides (e.g., tetrabutyl titanate), titanium(IV) phosphate, zirconium alkoxides, zinc acetate, lead acetate, cobalt acetate, manganese(II) acetate, antimony trioxide, germanium oxide, or the like, and mixtures thereof. Catalysts that do not significantly promote isocyanate reaction chemistries are preferred. The amount of catalyst used is typically in the range of 0.005 to 5 wt. %, preferably 0.01 to 1 wt. %, more preferably 0.02 to 0.7 wt. %, based on the total amount of polyol being prepared.

The hydrolysis and chemolysis of the digestible keratin source can be catalyzed by the use of enzymes such as proteases; lipases; amylases; maltases; sucrases; lactases; esterases; hydrolases; amidases; glycosidases; glycoside hydrolases; peptidases and the like and mixtures thereof. Subsequent reaction of the resulting hydrolysis or chemolysis products with the digested intermediate may then be facilitated by enzymes such as lipases; amidases and esterases.

The reaction can also be catalyzed by the use of acids or bases, including carboxylic acids.

The digestion of keratin by the glycol can also be catalyzed by the use of sulfites such as, for example, sodium sulfite, sodium metabisulfite, potassium metabisulfite, sodium hydrogen sulfite, calcium hydrogen sulfite, and potassium hydrogen sulfite, and combinations thereof.

Polyols from a Second Reaction Step

In a further second reaction step, the digested keratin source can be condensed with a digestible aromatic source to provide a polyol.

The weight percent of keratin source in the resulting polyol product is generally greater than about 3% by weight.

In another aspect, the keratin-derived polyol is made in a single step, or one pot reaction, by reacting the keratin and glycol under conditions effective to produce the keratin-derived polyol. As with polyols made using the two-step process, the weight percent of keratin-derived material in the resulting polyol product after digestion is greater than about 3% by weight, and the resulting polyol has a hydroxyl number within the range of 10 to 800 mg KOH/g. When the single-step process is used, it is preferred to utilize a condensation system that returns glycols to the reaction vessel while allowing removal of water, as removal of too much glycol can result in cloudy or opaque polyols.

The inventive keratin-derived polyols have hydroxyl numbers within the range of 10 to 800 mg KOH/g, preferably 25 to 500 mg KOH/g, more preferably 35 to 400 mg KOH/g, and yet more preferably 50 to 400 mg KOH/g. Hydroxyl number can be measured by any accepted method for such a determination, including, e.g., ASTM E-222 ("Standard Test Methods for Hydroxyl Groups Using Acetic Anhydride Acetylation").

The inventive keratin-containing polyols preferably have average hydroxyl functionalities (i.e., the average number of —OH groups per molecule) within the range of 1.5 to 6.0, more preferably 1.8 to 4.5, and most preferably 2.0 to 4.0.

The inventive polyols are flowable liquids at temperatures between 20° C. and 125° C. Preferably, the polyols have viscosities measured at between 25° C. and 125° C. of less than about 20,000 cP. In some embodiments, the polyols have a viscosity at 25° C. less than about 20,000 cP. In other embodiments, the polyols have a viscosity at 25° C. less than about 10,000 cP. In yet other embodiments, the polyols have a viscosity at 125° C. less than about 5000 cP. However, polyols outside these viscosity ranges can also be useful.

Viscosity can be determined by any industry-accepted method. It is convenient to use, for instance, a Brookfield viscometer (such as a Brookfield DV-III Ultra rheometer) fitted with an appropriate spindle, and to measure a sample at several different torque settings to ensure an adequate confidence level in the measurements.

The polyols preferably have low acid numbers. Urethane manufacturers will often require that a polyol have an acid number below a particular specification. Low acid numbers can be ensured by driving the condensation step (with digestible polymer) to the desired level of completion or by adding a neutralizing agent (e.g., sodium hydroxide) at the conclusion of the condensation step. Preferably, the polyols have an acid number less than 30 mg KOH/g, more preferably less than 10 mg KOH/g, and most preferably less than 5 mg KOH/g. As suggested above, it is acceptable practice to adjust acid numbers if necessary for a particular application with an acid scavenger such as, for example, an epoxide derivative, and this treatment can be performed by the manufacturer, distributor, or end user.

An advantage of the polyols is their reduced reliance on petrochemical sources for raw material. Preferably the poly has a keratin source content as defined herein greater than 3 wt %.

A desirable polyol attribute is the absence of settling, particularly upon prolonged storage. When settling is substantial, the polyol might have to be filtered, stirred, stirred with heating or otherwise treated to remove or redissolve the solids content; this is preferably avoided. Preferred inventive polyols exhibit no settling or only a slight degree of settling, and more preferred polyols exhibit no evidence of settling.

Products Prepared from Polyols

The inventive polyols can be used to formulate a wide variety of polyurethane products. By adjusting the proportion of digestible keratin source used, a desired degree of polyol hydrophobicity can be "dialed in." The ability to control hydrophobicity is particularly valuable in the coatings industry. The polyols can be used for cellular, microcellular, and non-cellular applications including flexible foams, rigid foams (including polyisocyanurate foams), urethane dispersions, coatings, adhesives, sealants, and elastomers. The resulting polyurethanes are potentially useful for automotive and transportation applications, building and construction products, marine products, packaging foam, flexible slabstock foam, carpet backing, appliance insulation, cast elastomers and moldings, footwear, devices, and other applications.

Further, the inventive keratin-containing polyols may be derivatized to form mono-, di- and polyacrylates via esterification or transesterification with acrylic acid or methacrylic acid-derived raw materials. Examples of (meth) acrylation raw materials suitable for forming (meth)acrylate derivatives of the inventive polyols include acryloyl chloride, methacryloyl chloride, methacrylic acid, acrylic acid, methyl acrylate, methyl methacrylate, and the like, or mixtures thereof. Such (meth)acrylate-derivatized inventive polyols are useful for radiation or UV-cure coating formulations or applications. Isocyanate prepolymers of the inventive polyols may be derivatized to form urethane (meth) acrylates via reaction with hydroxyethyl (meth)acrylate. The resulting urethane acrylates may also be used in radiation or UV-cure coating formulations or applications.

In a particular aspect, the invention relates to aqueous polyurethane dispersions made from the inventive keratin-containing polyols. Numerous ways to formulate aqueous polyurethane dispersions are known and suitable for use. Preferably, the polyurethane dispersion is made by emulsifying an isocyanate-terminated prepolymer having a keratin-derived polyol content in water with the aid of an emulsifying agent. Water, a water-soluble polyamine chain extender, or a combination thereof may be used to react with the emulsified prepolymer. The prepolymer is preferably made by reacting an inventive keratin-derived polyol, a hydroxy-functional emulsifier, one or more auxiliary polyols, and one or more polyisocyanates. The aqueous polyurethane dispersions are preferably used to formulate waterborne coatings, adhesives, sealants, elastomers, and similar urethane products, and they are particularly valuable for reducing reliance on solvents. For instance, the dispersions can be used to formulate low- or zero-VOC compositions.

Polyisocyanates suitable for use in making the prepolymers are well known; they include aromatic, aliphatic, and cycloaliphatic polyisocyanates. Examples include toluene diisocyanates (TDIs), MDIs, polymeric MDIs, naphthalene diisocyanates (NDIs), hydrogenated MDIs, trimethyl- or tetramethylhexamethylene diisocyanates (TMDIs), hexamethylene diisocyanate (HDI), isophorone diisocyanates (IP-DIs), cyclohexane diisocyanates (CHDIs), xylylene diisocyanates (XDI), hydrogenated XDIs, and the like. Aliphatic diisocyanates, such as hexamethylene diisocyanate and isophorone diisocyanates are particularly preferred.

Auxiliary polyols suitable for use are also well known. They include polyether polyols, aliphatic polyester polyols, aromatic polyester polyols, polycarbonate polyols, glycols, and the like. Preferred auxiliary polyols have average hydroxyl functionalities within the range of 2 to 6, preferably 2 to 3, and number average molecular weights within the range of 500 to 10,000, preferably 1,000 to 8,000. Preferred polyester polyols are condensation products of aromatic or aliphatic diacids and diols or triols (e.g., ethylene glycol, propylene glycol, 2-methyl-1,3-propanediol, 3-methyl-1,5-pentanediol, 1,4-butanediol, neopentyl glycol, glycerin, trimethylolpropane, 1,4-cyclohexanedimethanol, bisphenol A ethoxylates), especially diols.

A hydroxy-functional emulsifier is also used to make the polyurethane dispersions. The role of this component is to impart water-dispersibility to the prepolymer, usually upon its combination with water and a neutralizing agent, such as an acid or base reactant. Thus, in one aspect, the hydroxy-functional emulsifier is an acid-functional diol such as dimethylolpropionic acid (DMPA) or dimethylolbutanoic acid (DMBA). The acid functionality in the resulting prepolymer allows for neutralization with an amine or other basic reactant to generate a water-dispersible urethane. The hydroxy-functional emulsifier can also be an amine, such as N-methyldiethanolamine. Neutralization of the resulting prepolymer with an acidic reagent renders it water dispersible. In other aspects, the hydroxy-functional emulsifier is nonionic, e.g., a polyethylene glycol monomethyl ether. In another aspect, the hydroxy-functional emulsifier may be a monol- or diol-functionalized poly(ethylene oxide), such as for example Ymer™ N120 dispersing monomer (product of Perstorp), polyethylene glycols, or the methyl ether of polyethylene glycol. Additionally, non-reactive, so-called "external emulsifiers," such as the triethanolamine salt of dodecylbenzene sulfonic acid, may be included in the aqueous phase to assist in the emulsification and stabilization of the prepolymer and resulting polyurethane dispersion.

In certain aspects, a chain terminator may be used to control the molecular weight of the polyurethane polymer contained within the aqueous polyurethane dispersion. Monofunctional compounds, such as those containing hydroxyl, amino, and thio groups that have a single active hydrogen-containing group, are suitable chain terminators. Examples include alcohols, amines, thiols, and the like, especially primary and secondary aliphatic amines.

Chain extenders can also be included in making the polyurethane dispersion. In some aspects, the chain extender is added in an amount sufficient to react 5 to 105 mole % of free NCO groups present. Suitable chain extenders contain at least two functional groups that are capable of reacting with isocyanates, e.g., hydroxyl, thio, or amino groups in any combination. Suitable chain extenders include, for example, diols (ethylene glycol, propylene glycol, diethylene glycol, neopentyl glycol, 1,4-butanediol, 2-methyl-1,3-propanediol, 3-methyl-1,5-pentanediol, 1,4-cyclohexanedimethanol, and the like), di- and polyamines (ethylenediamine, diethylenetriamine, Jeffamine® T-403, Jeffamine® D-230, Jeffamine® ED-2001, Jeffamine® ED-600, Jeffamine® ED-900, 1,6-hexamethylenediamine, butylenediamine, hydrazine, piperazine, N-hydroxyethyl ethylenediamine) alkanolamines (ethanolamine, diethanolamine, N-methyl diethanolamine, and the like), dithiols, and the like. Diol chain extenders are preferably added during the preparation of the prepolymer, and prior to emulsification in water.

For more examples of suitable approaches for preparing aqueous polyurethane dispersions, see U.S. Pat. Nos. 5,155,163; 5,608,000; 5,763,526; 6,339,125; 6,635,723; 7,045,573; and 7,342,068, the teachings of which are incorporated herein by reference.

Coatings

The polyester polyols of the present invention are useful for making coatings. A coating is a covering that is applied to the surface of an object, which usually referred to as the substrate. The coatings typically comprise from about 1% to about 95%, by weight of the polyester polyol, preferably from about 2% to about 90% by weight of the polyester polyol, and more preferably from about 5% to about 80% by weight of the polyester polyol. The optimum weight percentage of the polyester polyol can be determined by one of skill in the art to obtain the desired property of the coating both before and after application to the substrate. Both liquid coatings and powder coatings can be made with the polyols of the present invention. Examples of liquid coatings include polyurethane coatings. These liquid coatings can include additional components such as catalysts, flow and leveling agents, surface modifying additives, wetting agents, dispersing agents, foam-control agents, solvents, crosslinking additives, co-blended resins to modify properties, pigments and colorants, and degassing agents.

Powder coatings provide an important alternative to liquid coatings. These coatings can be prepared from resins, pigments, and additives. The powder is applied to a substrate, usually metal, and fused to form a continuous film by baking the coated metal, or by applying the powder coating to a heated substrate. The powder coatings typically have a glass transition temperature, $T_g$, greater than or equal to 45° C., preferably greater than or equal to 50° C., and more preferably greater than or equal to 55° C. The powder coatings also typically have a melting point greater than or equal to 45° C., preferably greater than or equal to 50° C., and more preferably greater than or equal to 55° C. The glass transition temperature and the melting point of the powder coating can be adjusted by the selection of the polyester polyol or polyols incorporated, as well as the weight percentage of the polyol or polyols in the coating. It is highly desirable to adjust the glass transition temperature and melting point such that the powder coating remains as a free flowing powder at room temperature and elevated storage conditions, such as for example in a hot warehouse, but also readily melts to form a uniform coating on a substrate that has either been preheated before application of the powder coating or that is subsequently baked after application of the powder coating. While it is important to maintain a high enough glass transition temperature and melt temperature to prevent sintering, it is desirable to simultaneously tune the powder coating such that the optimal melt flow and crosslinking temperature is as low as possible, which results in a lower, narrower process window for films. This lower temperature is advantageous from an energy savings standpoint to the applicator. Additives are an important ingredient in the formulation of powder coatings. For the most part, additives perform the same functions in powder coatings as in liquid coatings. With the exception of wetting, dispersing and foam-control agents, many of the same additives used in liquid coatings are also used in powders. The powder coatings can comprise additional components such as crosslinking agents, flow control agents, degassing agents, catalysts, and pigmenting materials. The powder coatings can be applied to a metal substrate using conventional techniques known in the art such as electrostatic spraying. The metal substrate can either be preheated before application of the powder coating or baked after the application of the powder coating to thermally set the coating.

See U.S. Pat. No. 5,637,654, to Panandiker et al, issued Jun. 10, 1997; U.S. Pat. No. 4,197,353, to Tobias et al, issued Apr. 8, 1980; PCT Patent Application No. WO 2011/138432 A1, to DSM IP Assets, B. V., published Nov. 10, 2011; and "Organic Coatings Science and Technology", 3rd Ed., Wiley, 2007, Z. Wicks, Jr., F. Jones, S. P. Pappas, D. A. Wicks, Chapter 28.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

"Recycle content" as used herein (wt. %) is determined by combining the masses of recycled glycol, recycled aromatic polyacid source, recycled hydrophobe, and recycled digestible polymer, and dividing this sum by the total mass of reactants, and then multiplying the result by 100.

Hydroxyl numbers or values (OHVs) and acid numbers or values are determined by standard methods (ASTM E-222 and ASTM D3339, respectively) and reported as mg KOH/g. Viscosities are measured at 25° C. using a Brookfield DV-III Ultra rheometer with spindle #31 at 25%, 50%, and 75% torque, with 50% torque being the usual torque setting. Alternatively, depending on the viscosity of the sample, viscosities can also be measured at other temperatures, including up to about 50° C. or higher. Also, viscosities can be determined on diluted samples. Color, clarity, and degree of settling are evaluated visually.

Examples I to V provide procedures for carrying out the indicated digestion processes on the keratin source. Example VI provides a procedure for making coatings from the keratin-derived polyols. Example VII provides a procedure for making a polyurethane foam from the keratin-derived polyols. Table 1 summarizes data of the digestion products of the keratin sources. Table 2 summarizes testing data on coatings made from the keratin-derived sources.

Example I

Digestion of Chicken Down Feathers

A 500 mL reactor equipped with an overhead mixer, condenser, heating mantle, thermocouple, and nitrogen inlet is charged with 202.75 g of diethanolamine, and 24.56 g of chicken feathers. The temperature was raised to 186° C. with stirring. Reflux was observed and the temperature was raised to 220° C. A Dean Stark trap was added to collect the refluxing liquid. After about 3 hours, the chicken feathers had completely digested, and the reaction was cooled to 100° C. This dark brown polyol (Polyol Example 5 in Table 1) yielded an acid value of 4.3 mg KOH/g, an OHV of 322.3, a viscosity of 3488 cP at 25° C. and no settling after several days.

Example II

Digestion of Goose Down

A 1 L reactor equipped with an overhead mixer, condenser, heating mantle, thermocouple, and nitrogen inlet is charged with 351.1 g of diethylene glycol, followed by eleven additions of goose down at a reaction temperature of 180-185° C., each averaging 26.04 g over the course of the next 23 hours. Prior to each addition, the reaction mixture was inspected visually prior to adding another aliquot of goose down to insure that the previous addition had undergone full digestion and dissolution.

At this point, the polyol was cooled to 121° C. and 299.3 g of the product were removed from the reactor. This dark brown polyol (Polyol Example 2 in Table 1) yielded an acid value of 25.7 mg KOH/g, an OHV of 622.1, a viscosity of 3488 cP at 25° C. and no apparent settling after several days at room temperature.

Example III

Incorporation of a Hydrophobe into a Keratin Derived Polyol

The polyol from Example II was further reacted to incorporate a hydrophobe. A Dean Stark trap was connected to the reactor and ricinoleic acid (40% by wt. based on the remaining polyol remaining in the reactor) was added. The contents were heated with stirring to 185° C. for 2.6 hours. This dark brown polyol (Polyol Example 3 in Table 1) yielded an acid value of 14.0 mg KOH/g, an OHV of 369.9, a viscosity of 980.2 cP at 25° C. and no apparent settling after several days at room temperature.

Example IV

Digestion of Goose Down

For this digestion, a procedure similar to that of Example II was used for, except that the goose down was added together with the diethylene glycol in a single addition, followed by stirring at between 180 and 200° C., resulting in a solid (at 25° C.) dark brown, polyol (Polyol Example 4 in Table 1) with an acid value of 2.5 mg KOH/g, and a hydroxyl value (OHV) of 472.1 mg KOH/g.

Example V

Digestion of Chicken Feather Meal

A 500 mL reactor equipped with an overhead mixer, Vigreux column, short path condenser head with distillation collection flask, heating mantle, thermocouple, and nitrogen inlet was charged with 101.46 g of recycled diethylene glycol, 27.95 g of chicken feather meal, and 0.30 g titanium tetrabutoxide (~0.1% by wt.) and heated with stirring to 210° C. for 3 hr. After about 2 hours, the chicken feather meal had completely dissolved and appeared to be completely digested. The mixture was heated until no particles of chicken feather meal remained (about 2.5 hr). When the digestion reaction was considered complete, the mixture was cooled to about 100° C. 98.00 g of soybean oil and 25.00 g of phthalic anhydride were added, while the mixing rate was increased to 200 rpm. When the addition was complete the mixture was then heated to 215° C. Water generated in the condensation reaction was collected in the distillation flask until roughly the theoretical amount was removed. When the reaction was complete, the digested intermediate was allowed to cool to 100° C. and then decanted from the reactor. Any residual particles were removed by filtration through cheesecloth. The resulting opaque dark black-brown polyol (Polyol Example 6 in Table 1) had an acid value of 6.1 mg KOH/g, an OHV (hydroxyl value) of 351.6 mg KOH/g of sample, and a viscosity at 25° C. of 196.5 cP (centipoise).

Using the above procedure of this Example V, a further polyol was prepared using: 44% diethylene glycol, 1% glycerol, 31.9% phthalic anhydride, 11% soy bean oil, 0.1% Ti(IV)Bu Catalyst, and 12% chicken feather mea. The data for the polyol is presented (Polyol Example 7 in Table 1).

Example VI

Procedure for Preparing Polyurethane Coatings

A keratin-derived polyol, for example as from any of the previous Examples 1-V, can be used to prepare a polyurethane coating. The keratin-derived polyol (14.47 g, 0.0954 equiv.), 2-methyol-1,3-propanediol (0.70 g, 0.0156 equiv.), and ethylene glycol (1.09 g, 0.0363 equiv.) were added to an 250 mL beaker, at room temperature. Hexamethylene diisocyanate (8.76 g, 0.1042 equiv.) and isophorone diisocyanate (4.96 g, 0.0446 equiv.) were then added to the beaker. The mixture was then diluted to 50% by weight with 2-butanone. Mechanical mixing was initiated using a tri-lobe agitation blade measuring 3 inches in diameter and mixing was gradually increased until 500 RPM was reached and a homogeneous mixture resulted. Dibutyltin dilaurate (0.05% by wt.) was then added to the reaction mixture. After approximately 5 minutes of reaction time and ensuing 10° C. exotherm, a bead of the reacting mixture was applied to one side of each of five aluminum panels measuring 4 in. by 6 in. The beads of solvent-borne polyurethane were then drawn down each panel into a wet film using a #50 R.D. Specialties drawdown bar to a wet film thickness of 4.5 mils. The panels were allowed to flash dry in a hood at ambient temperatures for at least one hour, and then heated to 110° C. for 1.5-2 hours to permit complete conversion to polyurethane.

The final dry film thickness was determined using a PosiTector 6000 (Defelsko Corporation) dry film thickness gage. Konig hardness was measured using ISO 1522 using a TQC Pendulum Hardness Tester (Model SPO500). Pencil scratch hardness was measured using ASTM D3363. Flexibility was measured using ASTM D522. Adhesion was measured using ASTM D3359. Stain testing was measured using ASTM D1308. Methyl ethyl ketone (MEK) double rub testing was conducted using ASTM D4752. The results of the coating testing are summarized in Table 2 for coatings made from the polyols of Examples II and III.

Example VII

Procedure for Preparing a Polyurethane Foam

A rigid polyurethane foam was prepared using the polyol of Example V, above. The foam is prepared by the mixing of two components, Part A and Part B, where Part A is added to part B. Part A was made of Papi 27 (Dow Chemical). Part B was made up in a plastic beaker measuring 6" in diameter by 5" tall by mixing the keratin-based polyol of Example V with Fyrol PCF (Israel Chemical Ltd.), Dabco K-15 (Air Products), Polycat 5 (Air Products), Tegostab B8465 (Evonik), water, and n-pentane until homogeneous. Part A was then quickly added in a weight ratio of 1.141 A/B. Immediately after addition of Part A to Part B, the container was placed on a VOS power control mixer (VWR International) equipped with a 3 inch diameter Cowles blade and mixed at up to 2000 RPM for ten seconds. The mixing time was controlled by an electronic timer with foot pedal attachment (GraLab Model 451). Immediately after mixing was stopped, the resultant foam was poured into a 12"×12"×12" cardboard box and allowed to rise. After fully curing under ambient conditions, the foam was tested for compressive strength (ASTM D1621) and thermal conductivity (ASTM C177). Compressive strength was measured at 19.21 psi and thermal conductivity was 0.185 BTU*in/hr*ft$^2$*F (British thermal units "times" inches "per" hour "times" square feet "times" degrees in Fahrenheit).

TABLE 1

Characteristics of the Digested Keratin Source

| Polyol Example No. | Keratin Source | Wt. % Keratin | Glycol or Alkanol Amine | Catalyst | Acid Value mg KOH/g | OHV (mg KOH/g) | Color | Settling | Clarity | Viscosity (cP) at 25° C., unless noted 50% Torque, unless noted |
|---|---|---|---|---|---|---|---|---|---|---|
| 1 | Goose Down Feathers | 4.67% | Diethylene Glycol | None | 3.1 | 1000.2 | Dark red-brown | None | | 42 (35% torque) |
| 2 | Goose Down Feathers | 44.93% | Diethylene Glycol | None | 25.7 | 622.1 | Dark brown/black | None | Dark | 3488 |
| 3 | Goose Down Feathers | 37.07% | Diethylene Glycol/ 40 wt.% Ricinoleic Acid | None | 14.0 | 369.9 | Dark brown/black | None | Dark | 980.2 |
| 4 | Goose Down Feathers | 49.55% | Diethylene Glycol | None | 2.5 | 472.1 | Dark brown/black | Solidified at room temp. | Dark | — |
| 5 | Chicken Feathers | 10.80% | Diethanolamine | None | 4.3 | 322.3 | Dark brown/black | None | Dark | 3488 |
| 6 | Chicken Feather Meal | 12.00% | Diethylene Glycol | 0.10% Ti(BuO)$_4$ | 6.1 | 351.6 | Brown | None | Dark | 196.5 |
| 7 | Chicken Feather Meal | 12.00% | Diethylene Glycol | 0.10% Ti(BuO)$_4$ | 5 | 261 | Brown | None | Dark | 2772 |

TABLE 2

Physical Characteristics of Coatings Made from Digestible Keratin Sources

| Coating Example | Keratin-Derived Polyol | Coating Thickness, mil. | Konig Pendulum Hardness, Avg. Oscillations | Konig Pendulum Hardness, Avg. Sec. | Pencil Hardness, Avg. | Adhesion, Avg. | 1 hr. Mustard Resistance | 1 hr. Sunscreen Resistance | 1 hr. Windex Resistance | 1 hr. 100 proof Vodka Resistance | MEK Double Rubs | 1/8" Mandrel Test |
|---|---|---|---|---|---|---|---|---|---|---|---|---|
| 1 | Goose Down Feathers, Polyol from Example 2 from Table 1 | 2.19 | 60 | 85.4 | H | 5B | 5 | 5 | 5 | 2 | 92 | F |

TABLE 2-continued

Physical Characteristics of Coatings Made from Digestible Keratin Sources

| Coating Example | Keratin-Derived Polyol | Coating Thickness, mil. | Konig Pendulum Hardness, Avg. Oscillations | Konig Pendulum Hardness, Avg. Sec. | Pencil Hardness, Avg. | Adhesion, Avg. | 1 hr. Mustard Resistance | 1 hr. Sunscreen Resistance | 1 hr. Windex Resistance | 1 hr. 100 proof Vodka Resistance | MEK Double Rubs | 1/8" Mandrel Test |
|---|---|---|---|---|---|---|---|---|---|---|---|---|
| 2 | Goose Down Feathers, Polyol from Example 3 from Table 1 | 1.99 | 3 | 3.6 | H | 5B | 3 | 3 | 3 | 2 | 11 | P |

INCORPORATION BY REFERENCE

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

What is claimed is:

1. A keratin-derived polyol comprising recurring units of:
   (a) a digesting material selected from (i) an alkanolamine, (ii) a polyamine, or combinations thereof, and
   (b) an intermediate made by digesting a keratin source, wherein the digesting material and the keratin source are heated.

2. A keratin-derived polyol comprising recurring units generated from:
   (a) a digesting material selected from (i) an alkanolamine, (ii) a polyamine, or combinations thereof, and
   (b) a keratin source, wherein the digesting material and the keratin source are heated.

3. A keratin-derived polyol made by a process comprising heating a digesting material selected from (i) an alkanolamine, (ii) a polyamine, or combinations thereof, with a keratin source.

4. A keratin-derived polyol according to claim 1 wherein the alkanolamine is selected from ethanolamine, diethanol amine, triethanol amine, N-alkyl diethanolamine, isopropanolamine, diisopropanol amine, triisopropanol amine, N-alkyl diisopropanol amine, N-alkyl ethanolamine, 1,4-bis(2-hydroxyethyl)piperazine, 1-(2-hydroxyethyl)piperazine, fatty alkyl alkanol amines, 1-(2-(n,n-bis-(2-hydroxypropyl)-amino)-ethyl)-4-(2-hydroxypropyl)-piperazine, 1,4-bis(2-hydroxypropyl)piperazine, mono or polyalkoxylates of ethylene diamine, N,N-bis(2-hydroxyethyl)ethylenediamine, N,N,N,N-tetrakis(2-hydroxyethyl)ethylenediamine, alkoxylates of hexanediamine, alkoxylates of polyamines, alkoxylates of butanediamine, 1-(2-hydroxypropyl)piperazine, alkoxylates of toluene diamine, alkoxylates of aniline, alkoxylates of methylene dianiline, Mannich polyols by the Mannich reaction between a phenol or alkyl phenol, formaldehyde and alkanol amines, alkoxylates of melamine, and Mannich polyols obtained by the reaction of melamine with formaldehyde and a dialkanolamine, and combinations thereof.

5. A keratin-derived polyol according to claim 1 wherein the polyamine is selected from ethylene diamine, diethylene triamine, triethylene tetraamine, tetraethylene pentaamine, piperazine, 1-(2-aminoethyl)piperazine, polyoxyalkyleneamines 1,4-bis(2-aminoethyl)piperazine, butanediamine, hexanediamine, dimer diamine diaminocyclohexane, norbornane diamine, 1,12-dodecanediamine, 1,10-decanediamine, isophorone diamine, and diethyl toluene diamine, and combinations thereof.

6. A keratin-derived polyol according to claim 1 wherein the keratin source is selected from avian feathers, wool, and combinations thereof.

7. A keratin-derived polyol according to claim 6 wherein the keratin source is selected from avian feathers.

8. A keratin-derived polyol according to claim 7 wherein the keratin source is obtained from feather meal.

9. A keratin-derived polyol according to claim 7 wherein the avian feathers are selected from chicken feathers, chicken down feathers, turkey feathers, turkey down feathers, duck feathers, duck down feathers, goose feathers, and goose down feathers, and combinations thereof.

10. A keratin-derived polyol according to claim 9 wherein the avian feathers are chicken feathers.

11. A keratin-derived polyol according to claim 1 wherein the keratin source and the digesting material selected from (i) an alkanolamine, or (ii) a polyamine are heated at a temperature within the range of about 70° C. to about 240° C.

12. A keratin-derived polyol according to claim 1 having a hydroxyl number within the range of about 10 to about 800 mg KOH/g.

13. A keratin-derived polyol according to claim 1 having an acid number of less than 10 mg KOH/g.

14. A keratin-derived polyol according to claim 1 having a keratin source content greater than 3 wt %.

15. A keratin-derived polyol according to claim 1 further comprising a hydrophobe or nonionic surfactant, or combinations thereof.

16. A keratin-derived polyol according to claim 15 wherein the hydrophobe or nonionic surfactant is selected from ricinoleic acid, castor oil, ethoxylated castor oil, saturated or unsaturated C9-C18 dicarboxylic acids, vegetable oils, fatty acids, fatty acid esters, modified vegetable oils, fatty triglycerides, cardanol-based products, recycled cooking oil, isostearyl alcohol, hydroxy-functional materials derived from epoxidized, ozonized, or hydroformylated fatty esters, dimer fatty acids, block copolymers of ethylene oxide with propylene oxide, alkoxylated alkyl phenols, alkoxylated fatty alcohols, and combinations thereof.

17. A keratin-derived polyol according to claim 1 comprising a digesting material selected from (i) an alkanolamine.

18. A keratin-derived polyol according to claim 1 comprising a digesting material selected from (ii) a polyamine.

* * * * *